United States Patent [19]

Lehner

[11] Patent Number: 5,352,446
[45] Date of Patent: Oct. 4, 1994

[54] METHOD OF TREATING DENTAL CARIES WITH MONOCLONAL ANTIBODIES AGAINST THE ANTIGEN I AND ANTIGEN I/II OF STREPTOCOCCUS MUTANS

[75] Inventor: Thomas Lehner, Barnet, England

[73] Assignee: Council of Governors of the United Medical and Dental Schools of Guy's and St. Thomas's Hospitals, London, England

[21] Appl. No.: 983,273

[22] Filed: Nov. 30, 1992

Related U.S. Application Data

[63] Continuation of Ser. No. 841,783, Mar. 2, 1992, abandoned, which is a continuation of Ser. No. 616,829, Nov. 20, 1990, abandoned, which is a continuation of Ser. No. 120,690, Nov. 9, 1987, abandoned, which is a continuation of Ser. No. 843,690, Mar. 25, 1986, abandoned.

[51] Int. Cl.$^5$ .................... A61K 39/00; A61K 39/40
[52] U.S. Cl. ................... 424/150.1; 424/49; 530/388.4; 435/240.27
[58] Field of Search ............ 424/85.8, 87, 88, 92, 424/93 H, 49

[56] References Cited

U.S. PATENT DOCUMENTS

| | | | |
|---|---|---|---|
| 4,133,875 | 1/1979 | Hillman | 424/93 |
| 4,150,116 | 4/1979 | Taubman et al. | 424/88 |
| 4,324,782 | 4/1982 | Berk | 424/87 |
| 4,521,513 | 6/1985 | Russell | 424/87 |
| 4,594,244 | 6/1986 | Lehner et al. | 435/68 |
| 4,659,561 | 4/1987 | Fives-Taylor et al. | 424/92 |
| 4,693,888 | 9/1987 | Miyahara et al. | 424/88 |
| 4,741,999 | 5/1988 | Genco et al. | 530/387 |
| 5,240,704 | 8/1993 | Tsurumizu et al. | 424/85.8 |

FOREIGN PATENT DOCUMENTS 0038327 2/1985 Japan.
2060647 5/1981 United Kingdom.

OTHER PUBLICATIONS

Lehner et al. (1985) Infect. Immun. 50, 796–799.
Lehner et al. (1981) Infect. Immun. 34, 407–415.
Smith et al, Inf and Immunity 46, 1984, pp. 168–175.
Sevier et al, Clin. Chem 27(11) 1981, pp. 1797–1806.
Diamond et al JAMA 248, 1982, pp. 3165–3169.

Primary Examiner—Keith Baker
Attorney, Agent, or Firm—Oblon, Spivak, McClelland, Maier & Neustadt

[57] ABSTRACT

A method of combatting dental caries in a mammal comprises topical application to a surface of a tooth in the mammals mouth of a monoclonal antibody raised against antigen I or antigen I/II of *Streptococcus mutans* serotype c.

4 Claims, No Drawings

METHOD OF TREATING DENTAL CARIES WITH MONOCLONAL ANTIBODIES AGAINST THE ANTIGEN I AND ANTIGEN I/II OF STREPTOCOCCUS MUTANS

This application is a continuation of application Ser. No. 07/841,783, filed on Mar. 2, 1992, now abandoned which is continuation of Ser. No. 07/616,829, filed on Nov. 20, 1990, abandoned, which is a continuation of Ser. No. 07/120,690 filed Nov. 9, 1987, abandoned, which is a continuation of Ser. No. 06/843,690, filed Mar. 25, 1986, abandoned.

FIELD OF THE INVENTION

This invention relates to vaccines against dental caries.

BACKGROUND TO THE INVENTION

*Streptococcus mutans* has been recognised for many years as the major organism responsible for the development of dental caries in mammals. Various vaccines have been proposed in the past based on various antigenic fragments of *S. mutans*. One such vaccine is described in British Patent No. 2,060,647 based upon the antigen known as I or I/II. Antigen I has a molecular weight, as determined by sodium dodecyl sulphate polyacrylamide gel electrophoresis (SDS-PAGE) of 146-155 Kd. Antigen I/II is believed to be a conjugate of antigen I and antigen II, this I, II antigen having a molecular weight determined by SDS-PAGE of 175-195 Kd. U.S. patent application Ser. No. 579,117 now U.S. Pat. No. 4,594,244 describes antigen X which is a much smaller molecule having a molecular weight, determined by SDS-PAGE of about 3.5-4.5 Kd but which appears to include the same antigenic determinants included within antigens I and I/II.

Antibodies against antigens I, I/II and X are known. The above-mentioned British Patent describes the raising of antibodies against antigens I and I/II by conventional procedures in experimental animals, for example rhesus monkeys, rabbits and mice. These antibodies are proposed primarily for the purification of the antigen by affinity chromatography but the Patent Specification mentions the possibility of using such antibodies for passive immunisation by conventional means. Conventional passive immunisation involves parenteral administration of the antibodies but while such techniques are theoretically available, as a practical matter, passive immunisation has never been regarded as clinically attractive and indeed, the British Patent refers to the preferred use of the antigenic materials for direct immunisation.

Monoclonal antibodies against antigen I and antigen I/II are described in Smith et al, Infection and Immunity, Volume 46, No. 1, pages 168-175 (1984). This Paper describes the specificities of the various monoclonal antibodies by direct binding and inhibition with the pure streptococcal antigens with a solid phase radioassay. Conventional antisera to *S. mutans* serotype c, of the type described in the above-mentioned British Patent, cross-react with serotypes c, e and f (and g) while the monoclonal antibodies derived from antigen I/II of serotype c react predominantly with serotype c antigen and shows low titre reactivity with serotype f and possibly e. The slight cross-reactivity between *S. mutans* cells of serotype c and f could be further differentiated by absorption of any of the three monoclonal antibodies to I/II with cells of serotype c. Parallel studies of monoclonal antibodies with cells of *S. mutans* and their ammonium sulphate precipitated culture supernatants suggested that some antigenic determinants are retained predominantly on the cell surface but others are readily shed into culture medium so that they are detected both on the cell surface and in the culture medium. Unlike the polyclonal antibodies, the monoclonal antibodies are capable of discriminating single antigenic determinants and the Paper suggests that this can be applied to the study of the shedding of antigens from microorganisms into the environment such as the gut or gingival sulcus.

SUMMARY OF THE INVENTION

It has now been surprisingly found that the monoclonal antibodies against *S. mutans* antigens I and I/II can be effectively used topically in passive immunisation to provide inhibition of the development of *S. mutans* on the teeth of mammals for extended periods of time.

Accordingly, the present invention provides a method of combatting dental caries in a mammal which comprises topical application to a surface of a tooth in the mammal's mouth of a monoclonal antibody raised against antigen I or antigen I/II of *Streptococcus mutans* serotype c.

DETAILED DESCRIPTION OF THE INVENTION

While the present invention is directed primarily to humans, the problem of dental caries is not confined to humans but arises in other mammals including non-human primates, domestic and farm animals and particularly in those cases where the non-human mammal eats a substantial proportion of food including sugars.

The monoclonal antibodies used in this invention may be applied to the tooth in the mouth of the mammal by any convenient method. Numerous methods are now available for the treatment of teeth with various materials for various purposes. If the treatment is to be carried out by a Dental Surgeon, then the monoclonal antibody is conveniently applied by painting the surface of the tooth. If the monoclonal antibodies are to be self-applied, then the monoclonal antibodies may be included in a toothpaste, mouthwash, chewing gum, lozenge or gel. As will be described in more detail below, the duration of protection afforded by the method of the present invention is surprisingly long but the frequency of the topical application is primarily one for the users personal convenience. Methods of self-application from toothpastes etc., can result in applications being repeated perhaps daily while the use of lozenges can result in more frequent application of the antibody. Chewing gums and gels may be regarded, for this purpose, as providing a certain amount of sustained release of the antibody over a period of half-an-hour or more and indeed, if sustained release of the antibody is required, then appropriate formulations can be used that will result in slow release of antibody into the mouth from the formulation as a result of the temperature or saliva conditions etc., found in the mouth. In certain instances, it may be desirable to provide a more formal prolonged contact of the antibody with the tooth surface and in such cases, appropriate tooth masks can be used that will cover the tooth after it has been coated with antibody and prevent the antibody from being removed, e.g. by saliva, for a predetermined period.

It is important that the antibody be brought into contact with the surface of the tooth and ideally should be applied to all of the smooth and occlusal surfaces of the tooth. It is not detrimental for the antibody to contact the gum but the protection afforded by the present invention does appear to result primarily if not exclusively from the contact of the antibody with the surface of the tooth itself.

The exact amount of antibody that is applied does not appear to be critical since, in a method of this type, repeated self-application of antibody is not difficult and indeed, particularly after initial treatment by a Dental Surgeon, maintenance or top-up treatment can be carried out by the user at whatever frequency is desirable. By way of guidance, it can be indicated that somewhere of the order of 10 to 100 micrograms of antibody can be applied to each tooth on each occasion that antibody is applied but amounts of antibody outside this range can certainly be applied without causing detriment to the subject. The use of insufficient quantities of antibody simply means that the level of protection is not as great as would otherwise be obtainable while the use of excessive amounts of antibody does not improve the protection and simply results in unnecessary use of antibody.

The exact formulation for the antibody is not a matter of critical importance but depends entirely upon the method of application to be adopted and the convenience of the user. In all cases, it is important to formulate the antibody in an environment of appropriate pH and which is free from other deleterious materials which might bring about protein degradation and the formulation should, of course, also be free from microbial impurity that would be deleterious in the subject's mouth. For example, for use in the dental surgery, the antibody could be formulated as a simple aqueous dispersion containing somewhere in the region of 0.1 to 10 milligrams of antibody per 100 microlitres of liquid and a liquid of such concentration could be applied to the tooth at the rate of about 1 to 10 microlitres of dispersion per tooth. Where the antibody is to be formulated for self-administration, then the concentration can be selected bearing in mind the above guidelines, the quantities of the formulation that are normally taken on each occasion of self-administration and the fact that over administration of antibody will not be deleterious.

The monoclonal antibody to be used in this invention can be raised by conventional hybridoma technology. Thus, mice may be injected with the selected antigen I or antigen I/II as immunogen and spleen cells from the immunised mice subsequently fused with mouse myeloma cells by the techniques originally pioneered by Kohler & Milstein and the later developments thereof. Detailed procedures for the production of monoclonal antibodies that can be used in the present invention are set out in Smith et al Infection and Immunity, Volume 46, No. 1, pages 168-175 (1984), the disclosure of which is incorporated in this specification by this reference. Smith et al describes in Table 1 the production of four specific monoclonal antibodies, any of which are suitable for use in the present invention. Table 1 describes one IgG 1 antibody and two IgG 2a antibodies against antigen I/II that are coded 2B1, 2D4, and B4. A further IgG 1 antibody against antigen I is described and coded 6A6. Repetition of the detailed procedures described in Smith et al will result in the production of further monoclonal antibodies against antigen I and antigen I/II which, while, almost by definition, cannot be identical to the monoclonal antibodies described in Table 1, will be very similar to those antibodies and will behave immunogenically in an identical fashion.

One representative hybridoma produced by the techniques described in the Smith et al Paper, prepared from a mouse that has been immunised by antigen I/II has been deposited under the conditions of the Budapest Treaty with the European Collection of Animal Cell Cultures (ECACC) at the Public Health Laboratory Service Centre for Applied Microbiology and Research, Porton Down, Salisbury, Wiltshire, SP4OJG, England. The ECACC has been designated an International Depository Authority under the Budapest Treaty 1977. The deposit made in connection with this Patent Application was made on 19th Mar. 1986 and, has been given the Deposit Number 86031901.

SPECIFIC EMBODIMENTS

EXAMPLE 1

This Example describes the use of monoclonal antibodies to protect the teeth of rhesus monkeys. The test animals were 9 young rhesus monkeys having all their deciduous teeth but where none of their permanent teeth had erupted. The monkeys were fed on a human-type diet of sandwiches, eggs, bananas, oranges and about 15% sugar. It is well recognised that under these conditions, unprotected monkeys develop indigenous *S. mutans* serotype c in their dental plaque and that this leads to the development of dental caries.

The monkeys were protected with monoclonal antibody that was prepared by the procedure described by Smith et al, Infection and Immunity, Volume 46, No. 1, pages 168-175 (1984) where the immunogen used for the mice was antigen I/II of *S. mutans* serotype c. The material used for passive immunisation was whole ascites fluid. On each occasion that immunisation took place, the teeth of the monkeys was dried with gauze and about 100 microlitres (containing 1 mg of IgG) of monoclonal antibody was applied to the smooth and occlusal surfaces of all of the teeth (about 5 microlitres of monoclonal antibody per tooth). To avoid dilution and washing away of the monoclonal antibody by saliva, silicon rubber appliances, moulded to fit the teeth and gums of the individual monkeys, were fitted to their teeth and maintained with slight digital pressure for 5 minutes.

The group of 9 monkeys was divided into 5 control monkeys and 4 test monkeys. The test monkeys were immunised on 12 occasions throughout the test, at weekly intervals for the first 5 weeks with immunisation No. 6 at 7 weeks, No. 7 at 12 weeks, No. 8 at 18 weeks, No. 9 at 22 weeks, No. 10 at 25 weeks, No. 11 at 30 weeks and No. 12 at 38 weeks. On each occasion that the test monkeys were immunised, the 5 control monkeys had saline applied to their teeth.

The teeth were examined at about 2 monthly intervals with a probe and mirror as well as by X-rays. The mean ($\pm$ the standard error) number of carious lesions per animal is regarded as the caries score.

To determine the extent of development of *S. mutans*, dental plaque was collected separately from the smooth surfaces of the upper central incisors and from the fissures of the upper left second molar with sterile probes and placed into transport medium. The proportion of *S. mutans* grown on tryptone yeast extract - L-cystine medium was determined and expressed as a mean ($\pm$ the standard error) percentage of the total number of colonies grown on that medium.

The tests were carried out over a period of about one year and the results are shown in Tables 1, 2 and 3.

TABLE 1

| | Caries Score | | | | | | | |
|---|---|---|---|---|---|---|---|---|
| Time - Weeks | 0 | 8 | 16 | 20 | 28 | 32 | 36 | 48 |
| Immunised monkeys | 0 | 0 | 0 | 0 | 0 | 0 | 0 | 0 |
| Control monkeys | 0 | 0 | 0 | 0 | 1 | 1.8 | 3.0 | 3.0 |

TABLE 2

| | % S. mutans in fissures | | | | | |
|---|---|---|---|---|---|---|
| Time - Weeks | 0 | 12 | 20 | 28 | 36 | 48 |
| Immunised monkeys | 0 | 0 | 2 | 3 | 0 | 2 |
| Control monkeys | 0 | 30 | 27 | 21 | 21 | 20 |

TABLE 3

| | % S. mutans on smooth surfaces | | | | | |
|---|---|---|---|---|---|---|
| Time - Weeks | 0 | 12 | 20 | 28 | 36 | 48 |
| Immunised monkeys | 0 | 0 | 4 | 8 | 0 | 2 |
| Control monkeys | 0 | 30 | 31 | 42 | 32 | 31 |

DENTAL CARIES

The results show that the application of the monoclonal antibody to the deciduous teeth of the rhesus monkeys prevented the development of caries over a period of one year as compared with a mean (± the standard error) of 3.0 ± 2.0 carious lesions per control animal. There were 8 smooth surface and 7 fissure carious lesions in the control animals so that both smooth surface and fissure caries were prevented in the immunised animals. Caries was found in 3 of the control monkeys but in none of the passively immunised monkeys.

COLONISATION OF S. mutans

Colonisation of both smooth surfaces and fissures of teeth by S. mutans was significantly lower in those animals whose teeth were treated with the monoclonal antibody than in the untreated animals. The proportion of S. mutans in the fissures of teeth of control monkeys was between 21 and 31% as compared with 0-2% in immunised monkeys. The results for smooth surface plaque was similar, 30-44% in control monkeys and 0-8% in immunised monkeys.

EXAMPLE 2

Eight human patients had monoclonal antibodies (McAb; 2D4) or saline applied on three occasions (day 1, 2 and 5). The McAb 2D4 (an IgG2a material) was prepared to streptococcal antigen (SA) I/II according to Smith et al 1984 mentioned in Example 1. The mouse ascites fluid was purified by ammonium sulphate precipitation, followed by DEAE cellulose chromatography. The recovered protein was freeze-dried and reconstituted in PBS to a concentration of 10 mg/ml. This was centrifuged at 120,000 g for 30 minutes and passed through a 0.22 μm filter. The final preparation, stored at $-20°$ C., showed 6.8% binding to SA I/II and a titre of $10^{-6}$ in radioimmunoassay. Samples of 5 μl of McAb (or saline) were applied to the dried buccal and occlusal surfaces of each tooth on day 1, 2 and 5. Dilution or washing away by saliva was prevented, using custom made, silicone impression trays. The patients were asked to avoid eating, drinking and rinsing for the next 30 minutes. Implantation of Strep mutans was attempted on day 8, using $10^8 - 10^9$ per ml of a live, wild strain of streptomycin resistant Strep. mutans (K2). This was cultured in Todd Hewitt broth containing 1 mg/ml streptomycin, for 18 hours at 37° C. The resultant growth was centrifuged and washed twice in sterile phosphate buffered saline (PBS), and resuspended in PBS. The patients were asked to rinse with 10 ml of the Strep. mutans preparation, one hour after toothbrushing, and 2 minutes after rinsing with 10% sucrose.

Dental plaque samples were collected, from the smooth surfaces of the first incisors and first molars, and the fissures of the molars and pre-molars into a transport medium, (Bowden G. H. and Hardie J. M., 1971 "Anaerobic organisms from the human mouth" page 177 of Isolation of Anaerobes, SAB Technical Series No. 5, Soc. of Applied Bacteriology, London) at the intervals indicated. Unstimulated saliva was collected in cooled sterile tubes over a period of 4 minutes. The bacterial samples were plated, within one hour of collection, onto TYC agar (Lab M) with streptomycin (1 mg/ml), and blood agar in serial dilutions. In addition, saliva was plated onto TYC containing sucrose and bacitracin supplement. The TYC based plates were incubated for 72 hours at 37° C. under anaerobic conditions (Gaspak) and the blood based plated for 120 hours. The proportion of Strep. mutans was expressed as a percentage of the total colony count on the TYC medium. Serum, crevicular fluid and saliva were collected, before, during and after the experimental period, as described by Lehner et al Infection Immunity, Vol. 50, No. 3 pages 796–799 (1985). The samples were assayed for anti-SA I/II antibodies, by a solid phase radioimmunoassay (Smith and Lehner (1981), Clin, Exp. Immunol, 42, pages 417–424).

The results are set out in Table 4 and 5 below.

TABLE 4

| | % S. mutans in fissures | | | | | | | |
|---|---|---|---|---|---|---|---|---|
| Time-Days | 0 | 1 | 3/5 | 8/12 | 20/22 | 34/36 | 63/78 | 100/120 |
| Immunised subjects | 0.0 | 0.6 | 0.02 | 0 | 0.003 | 0 | 0 | 0.009 |
| Control subjects | 0.0 | 0.11 | 0.36 | 0.12 | 0.66 | 0.23 | 0.23 | 0.56 |

TABLE 5

| | % S. mutans on smooth surfaces | | | | | | | |
|---|---|---|---|---|---|---|---|---|
| Time-Days | 0 | 1 | 3/5 | 8/12 | 20/22 | 34/36 | 63/78 | 100/120 |
| Immunised subjects | 0.0 | 0.25 | 0.13 | 0.13 | 0.22 | 0.3 | 0.003 | 0.004 |
| Control subjects | 0.0 | 0.91 | 1.91 | 1.6 | 0.9 | 1.5 | 0.77 | 0.001 |

I claim:

1. A method of combatting dental caries in a mammal, which comprises topically applying to a surface of a tooth in the mouth of said mammal the monoclonal antibody produced by the hybridoma deposited in the European Collection of Animal Cell Cultures Under the Deposit No. 86031901.

2. The method according to claim 1, wherein the monoclonal antibody is painted onto the surface of the tooth.

3. The method according to claim 1, wherein the monoclonal antibody is applied to the surface of the tooth from a tooth paste, mouthwash, chewing gum, lozenge or gel.

4. The method according to claim 1, wherein about 10–100micrograms of antibody are applied per tooth on each application.

* * * * *